United States Patent [19]

Jones

[11] Patent Number: 4,599,373

[45] Date of Patent: Jul. 8, 1986

[54] AROMATIC OLIGOMERS AND RESINS

[75] Inventor: Michael E. B. Jones, Chester, England

[73] Assignee: Imperial Chemical Industries PLC, London, England

[21] Appl. No.: 725,347

[22] Filed: Apr. 19, 1985

Related U.S. Application Data

[62] Division of Ser. No. 558,525, Dec. 6, 1983, Pat. No. 4,530,992.

[30] Foreign Application Priority Data

Dec. 6, 1982 [GB] United Kingdom ............... 8234715
May 27, 1983 [GB] United Kingdom ............... 8314707

[51] Int. Cl.$^4$ ........................ A61K 6/08; A61K 5/04
[52] U.S. Cl. ............................. 523/116; 260/998.11; 523/117; 433/228.1
[58] Field of Search .................... 523/116, 117; 260/998.11; 433/228

[56] References Cited

U.S. PATENT DOCUMENTS

| | | | |
|---|---|---|---|
| 3,923,740 | 12/1975 | Schmitt et al. | 433/228 X |
| 4,177,563 | 12/1979 | Schmitz-Josten et al. | 523/117 X |
| 4,383,826 | 5/1983 | Butler et al. | 433/228 |
| 4,406,625 | 9/1983 | Orlowski et al. | 433/228 |
| 4,411,625 | 10/1983 | Koblitz et al. | 260/998.11 X |
| 4,490,115 | 12/1984 | Orlowski et al. | 523/117 X |

*Primary Examiner*—Lucille M. Phynes
*Attorney, Agent, or Firm*—Cushman, Darby & Cushman

[57] ABSTRACT

Compositions comprising an oligomer which (a) comprises the repeating unit (Ar - CHR), and where Ar is an aromatic group and R is hydrogen or a hydrocarbyl group or hydrogen, (b) has pendant and/or terminal groups which include inter alia acyloxymethyl, hydroxymethyl and carboxyl, and (c) has a functionality between 0.5 and 10, and processes for the preparation thereof are described. These compositions may be used in dental, electrical and electronic applications.

16 Claims, No Drawings

AROMATIC OLIGOMERS AND RESINS

This is a division, of application Ser. No. 558,525, filed Dec. 6, 1983, now U.S. Pat. No. 4,530,992, issued 7/23/85.

This invention relates to aromatic oligomers, to the preparation thereof, to resins prepared from compositions which comprise the oligomers and to filled and/or fibre-reinforced articles of the resins.

The reaction of diphenyl oxide, diphenyl sulphide, dibenzofuran and dibenzothiophene with formaldehyde in the presence of a carboxylic acid and catalytic quantities of a strong acid at reflux temperatures to give oligomers are known, for example as described in U.S. Pat. No. 3,914,194.

We have now found that where the molar ratio of strong acid to aromatic compound is at least 1:1 (a) the aforesaid reaction affords novel oligomers, (b) certain aromatic compounds which are less reactive than the aforesaid aromatic compounds can be used, and (c), where the carboxylic acid is an olefinically unsaturated carboxylic acid which is polymerisable by addition polymerisation (hereinafter referred to for convenience as "polymerisable olefinically unsaturated carboxylic acid") the reaction can be carried out at temperatures below 90° C. using commercially available grades of a polymerisable olefinically unsaturated carboxylic acid, which grades contain conventional amounts of stabiliser, often without the addition of further quantities of stabiliser. The presence of further quantities of stabiliser would reduce the ease with which such oligomers may be cured.

Compositions comprising the aforesaid oligomers may be converted into cured resins, either directly or via conversion into reactive intermediates. For example, where the pendant and/or terminal groups are acyloxymethyl groups in which the acyl portion is derived from a polymerisable olefinically unsaturated carboxylic acid curing may be effected in the presence of a suitable addition polymerisation initiator; where the pendant and/or terminal groups are acyloxymethyl groups in which the acyl portion is derived from an aromatic or aliphatic carboxylic acid curing may be effected by a suitable strong acid. The preparation and use of reactive intermediates is more fully described hereinafter. By careful selection of the structural features of the oligomers, cured resins having good combination of properties may be produced. The cured resins may provide the matrix for filled and/or fibre reinforced composites.

According to a first aspect of the present invention there is provided a composition comprising an oligomer, which may be linear or branched, which comprises the repeating unit —Ar[1]—CHR— and which has pendant and/or terminal groups, which groups, which may be the same or different, are acyloxymethyl, hydroxymethyl, carboxyl, 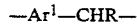

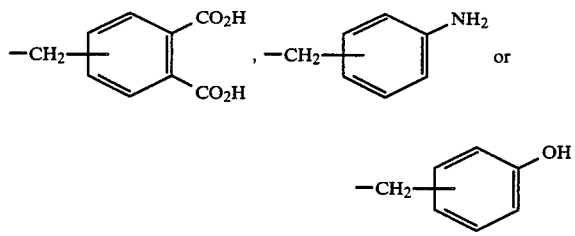

wherein Ar[1] is an aromatic group, or a substituted derivative thereof, each of which may be the same or different; R, each of which may be the same or different, is hydrogen, or a hydrocarbyl group and the average number of pendant and/or terminal groups, as hereinbefore defined, on each oligomer molecule (hereinafter referred to for convenience as "functionality") has a value between 0.5 and 10, with the proviso that where the aromatic group is a diphenyl oxide, diphenyl sulphide, dibenzofuran or dibenzothiophene residue, R is hydrogen and the pendant and/or terminal groups are acyloxymethyl and/or hydroxymethyl then the ratio of methylene groups which are attached to two aromatic groups at positions para to the heteroatoms in both aromatic groups (hereinafter referred to for convenience as "para-para linkages") to methylene groups which are attached to two aromatic groups at a position ortho to the heteroatom in one of the aromatic groups and at a position para to the heteroatom in the other aromatic group (hereinafter referred to for convenience as "ortho-para linkages") is less than 5:1.

In oligomers of which compositions according to the first aspect of the present invention are comprised the aforesaid ratio is preferably between 5:1 and 2:1. Oligomers having such ratios have less tendancy to crystallise than oligomers known in the art.

The aforesaid ratio may be determined by quantitative C[13]-nuclear magnetic resonance spectroscopy in which para-para linkages generate a signal at about 40 ppm and the ortho-para linkages generate a signal at about 35 ppm.

According to a second aspect of the present invention there is provided a process for the preparation of oligomers of which the compositions according to the first aspect of the present invention are comprised which process comprises at least the step of reacting an aromatic compound, an aldehyde and a carboxylic acid in the presence of a strong acid characterised in that the molar ratio of strong acid to aromatic compound is at least 1:1, with the proviso that where the carboxylic acid is a polymerisable olefinically unsaturated carboxylic acid the reaction is carried out at a temperature below 90° C.

In linear oligomers of which the compositions according to the first aspect of the present invention may be comprised it will be appreciated that each aromatic group may be bound into the oligomer backbone by bonds which may be ortho or para to each other. For example, where the aromatic group is derived from diphenyl oxide, backbone linkages such as

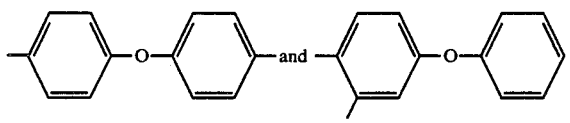

may be present.

The aromatic groups in an oligomer of which a composition according to the first aspect of the present invention is comprised may be mono-nuclear, e.g. as in phenylene; fused polynuclear, e.g. as in naphthalene or anthracene; or preferably have the structure —φ—Y$^1$—φ—. In —φ—Y$^1$—φ—, φ is the phenylene group and Y$^1$ is a direct link between the two phenylene groups; a divalent residue which includes one or more in-chain atoms, each of which atoms may be carbon or a hetero atom and may have one or more atoms appendant thereto, e.g. —O—, —S—, —CH$_2$— or a substituted derivative of —CH$_2$—, e.g. —C(CH$_3$)$_2$—; —CH$_2$CH$_2$—, and

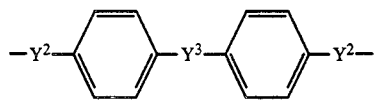

where Y$^2$, which may be the same or different, is a group which activates the aromatic nucleus to electrophilic attack, e.g. —O— and —S—, and Y$^3$ is a group which deactivates the aromatic nucleus to electrophilic attack, e.g. —SO$_2$— and —CO—.

Substituents which may be present on the aromatic groups include inter alia lower alkyl groups having up to five carbon atoms, e.g. methyl and ethyl; lower alkoxy groups e.g. methoxy; and halo groups, e.g. chloro.

Where the group R in the repeating unit —(Ar$^1$—CHR)— is a hydrocarbyl group it may be an aryl group, e.g. phenyl; an alkaryl group, e.g. tolyl; an aralkyl group, e.g. benzyl; or preferably an alkyl group having up to six carbon atoms, e.g. methyl or ethyl. We do not exclude the possibility that R may have one or more suitable substituents, e.g. halo groups. Preferably, however, R is a hydrogen atom.

Where the pendant and/or terminal groups on an oligomer of which the composition according to the first aspect of the present invention is comprised are acyloxymethyl groups the acyl portion thereof may be derived from inter alia an aliphatic carboxylic acid, an aromatic carboxylic acid, or preferably a polymerisable olefinically unsaturated carboxylic acid or a substituted derivative thereof. Where the acyl portion is derived from an aliphatic carboxylic acid or an aromatic carboxylic acid such oligomers have a slow rate of cure and liberate products which are volatile and/or toxic and/or corrosive and often difficult to remove completely; to obtain resins therefrom of high softening point, say above 100° C., high functionality oligomers are needed which, during curing, generate more byproducts, shrink, and tend to form voids and give brittle products.

As examples of suitable aliphatic and aromatic carboxylic acids from which the aforesaid acyloxymethyl groups may be derived may be mentioned formic, acetic, propionic, hexanoic, benzoic, and haloacetic, e.g. dichloroacetic, acids. Whilst it may be commercially attractive to employ an inexpensive carboxylic acid, e.g. acetic acid, it may be desirable, for example where the oligomer is to be used for the production of a substantially three-dimensional article to use a relatively involatile acid, for example having up to about eighteen carbon atoms, because in the curing of such an oligomer less pressure is required to overcome the problem of void formation during in-mould curing. Additionally, it will be appreciated that where a volatile carboxylic acid is evolved it is often preferred that it is not a noxious product such as dichloroacetic or trifluoroacetic acid.

As examples of suitable olefinically unsaturated carboxylic acids from which the aforesaid acyloxymethyl groups may be derived may be mentioned ethacrylic, crotonic, angelic, cinnamic, maleic, oleic and linoleic acids or preferably acrylic or methacrylic acid.

It will be appreciated that the functionality of oligomers of which the compositions according to the first aspect of the present invention are comprised will affect inter alia the viscosity and softening point of the oligomers and the mechanical properties of the cured resins prepared therefrom. It is often preferred that the functionality is between two and six. For example, where it is desired that a cured resin prepared from a composition according to the first aspect of the present invention has a softening point of at least 200° C. and the oligomer of which the composition is comprised has a number average molecular weight of about 1000, the oligomer preferably has a functionality of at least four; such cured resins are often able to withstand flash exposure, say of the order of a few minutes, to temperatures of about 270° C. It will be appreciated that where the molecular weight of the oligomer is greater or less than 1000 the functionality thereof has to be increased or decreased respectively t give a cured resin of softening point at least 200° C. The skilled man by simple experiment will be able to determine satisfactory number average molecular weight/functionality combinations for the oligomers.

As the number average molecular weight of an oligomer of which compositions according to the first aspect of the present invention are comprised increases, the viscosity of the oligomer increases and it becomes a viscous gum and then a solid. Above a number average molecular weight of about 1000, cohesive, tack-free films of oligomer can be obtained. Furthermore we have found that cohesive, tack-free films can be prepared from oligomers which have a number average molecular weight of less than about 1000 by dissolving therein certain polymers, i.e. so-called "polymeric binders", e.g. polystyrene, polyvinyl pyrrolidone, polyvinyl butyral, polyvinyl acetate, or polymethylmethacrylate or a polymer of the general formula

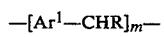   I where Ar$^1$ and R have the meaning hereinbefore ascribed to them and m is such that the number average molecular weight of the polymer of general formula II is more than 3000.

The aromatic compound used in the process according to the second aspect of the present invention may be mononuclear, e.g. as in benzene; fused polynuclear, e.g. as in naphthalene or anthracene; or preferably Ph—Y$^1$—Ph in which Ph is the phenyl group and Y$^1$ has the meaning hereinbefore ascribed to it. The aromatic compound may have substituents as hereinbefore described.

As examples of aldehydes which may be used in the process according to the second aspect of the present invention may be mentioned inter alia benzaldehyde, tolualdehyde, phenylacetaldehyde or preferably a lower alkyl aldehyde, e.g. acetaldehyde and propionaldehyde, more preferably, however, the aldehyde is formaldehyde.

Whilst we do not exclude the possibility that a solution of formaldehyde in, for example, water or methanol, may be used in the process according to the second aspect of the present invention, preferably the formaldehyde is in a solid form, e.g. paraformaldehyde, form or more preferably trioxane.

The carboxylic acid used in the process of the second aspect of the present invention is a hydrocarbyl carboxylic acid, which hydrocarbyl group may have one or more substituents and may be an alkyl, aryl, alkaryl, aralkyl or preferably an alkylene group. Examples of suitable carboxylic acids have been hereinbefore described. We have found that as the strength of the carboxylic acid is increased, e.g. dichloroacetic acid or trifluoroacetic acid, the reaction rate of the process is increased.

Where the carboxylic acid is methacrylic acid we have found that where it contains more than 500 ppm of methacrylamide there is a tendency for gelation and/or emulsification of the reaction mixture to occur when carrying out the process according to the second aspect of the present invention.

The strong acids used in the process according to the second aspect of the present invention have pKa's of less than 0.5.

As examples of strong acids which may be used in the process according to the second aspect of the present invention may be mentioned inter alia phosphoric acid, p-toluenesulphonic acid, trifluoromethane sulphonic acid, dichloroacetic acid, trifluoroacetic acid or preferably sulphuric acid. It will be appreciated that where the carboxylic acid used in the reaction is a strong acid as hereinbefore defined a portion thereof may serve as the strong acid.

In the process according to the second aspect of the present invention 1 mole of an aromatic compound is treated with about 1.0 to 15 moles of an aldehyde, about 5 to 40 moles of a carboxylic acid, and about 1 to 20 moles of strong acid. If too much strong acid is used it is difficult to control the exotherm and gelation occurs.

The reaction mixture used in the process of the present invention may include water. The water may be added as a discrete component of the reaction mixture or, where one of the reactants in the reaction mixture is used in the form of an aqueous solution, e.g. formalin and 85% sulphuric acid, at least a portion of the water is added as the solvent in the solution. The total amount of water added to the reaction mixture is typically less than 100 moles per mole of the aromatic compound.

Preferably the molar ratios of aromatic compound:aldehyde:carboxylic acid:strong acid:water which are used in the process of the present invention are 1:2-10:5-15:1-10:2-30 such ratios tend to decrease para-para:ortho-para ratio.

Conveniently the aromatic compound may be added to a mixture of the other reactants or the aldehyde may be added to a mixture of the other reactants.

A suitable inert diluent, e.g. 1,2-dichloroethane, or dioxan, may be present in the reaction mixture to increase the solubility of the aromatic compound therein. There is a tendency for such reaction mixtures to emulsify and hence the presence of a suitable inert diluent is often not preferred.

Where no inert diluent is present the process according to the second aspect of the present invention is preferably carried out between 50° C. and 90° C., more preferably at a temperature between 60° C. and 80° C.

The process according to the second aspect of the present invention may be carried out for between five minutes and twenty-four hours. Often substantially all the aromatic compound has reacted within a few hours.

Oligomers of which compositions according to the present invention are comprised may contain in-chain —OCHR— groups. Where it is desired to reduce, at least, the number of in-chain —OCHR— groups, the reaction may be continued for an extended period of time, e.g. up to, say, about 24 hours, and/or the ratios of aromatic compound:aldehyde:carboxylic acid:strong acid:water used in the reaction are 1:2-5:5-8:1-5:2-0. Where R is hydrogen the presence of in-chain —OCH$_2$— is indicated by the presence of one or more signals in the C$^{13}$-nuclear magnetic resonance spectrum of the oligomer.

When reaction is judged to be complete the product is treated to remove at least substantially all the strong acid, particularly where a polymerisable olefinically unsaturated acid is used in the process. The presence of residual strong acid can lead to the production of undesirable side products, with consequent decrease in properties, during production of a cured resin from the oligomer. Removal of the strong acid is conveniently effected by separating the inorganic phase from the organic phase and washing the organic phase with water, preferably hot water, a weakly alkaline solution, e.g. sodium bicarbonate, and then water.

An oligomer of which a composition according to the first aspect of the present invention may be comprised which has pendant and/or terminal hydroxymethyl groups may be prepared by hydrolysis of an appropriate oligomer in which the pendant and/or terminal groups are acyloxymethyl groups. Preferably hydrolysis is effected under basic conditions.

An aligomer of which a composition according to the first aspect of the present invention is comprised which has pendant and/or terminal carboxylic groups may be prepared by oxidation, with a suitable oxidising agent, e.g. chromic acid or potassium permanganate, of an appropriate oligomer which has one or more pendant and/or terminal acyloxymethyl or hydroxymethyl groups. Where the oligomer which is to be oxidised has at least one methylene group in the backbone thereof the oxidising agent is preferably strong enough to oxidise the at least one methylene group to at least one keto group and more preferably is potassium permanganate; cured resins prepared from oligomers with in-chain keto groups instead of in-chain methylene groups or more stable thermally.

An oligomer of which a composition according to the first aspect of the present invention is comprised which has pendant and/or terminal

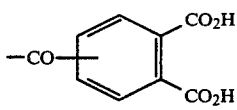

groups may be prepared by reacting an appropriate oligomer which has pendant and/or terminal acyloxymethyl or hydroxymethyl groups with an excess of o-xylene and Lewis acid catalyst, e.g. BF$_3$, to form an oligomer which has pendant and/or terminal

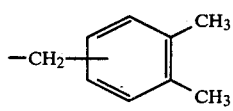

groups, the methyl groups of which may be oxidised with a suitable oxidising agent, e.g. potassium permanganate to form a group

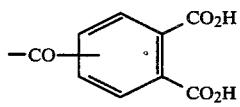

An oligomer of which a composition according to the first aspect of the present invention is comprised which has pendant and/or terminal

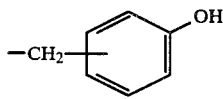

groups may be prepared by reacting an appropriate oligomer which has pendant and/or terminal hydroxymethyl and/or acyloxymethyl groups with a phenol. Typically the reaction is carried out by heating the oligomer which has pendant and/or terminal acyloxymethyl and/or hydroxymethyl groups with one or more molar equivalents of a phenol for each acyloxymethyl or hydroxymethyl group present in the presence of a suitable catalyst, e.g. toluene-sulphonic acid.

An oligomer of which a composition according to the first aspect of the present invention is comprised which has pendant and/or terminal

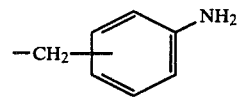

groups may be prepared by reacting an appropriate oligomer which has pendant and/or terminal hydroxymethyl groups with an aniline. Typically the reaction is carried out by heating the oligomer which has pendant and/or terminal hydroxymethyl groups with one or more molar equivalents of an aniline for each hydroxylmethyl group present.

Where oligomers of which compositions according to the first aspect of the present invention are comprised have pendant and/or terminal acyloxymethyl groups in which the acyl group is derived from a polymerisable olefinically unsaturated carboxylic acid they may be copolymerised with a suitable polymerisable olefinically unsaturated comonomer, e.g. an acrylate or methacrylate, or where the oligomer is a liquid, homopolymerised. Polymerisation may be effected by any of the techniques conventionally used in the addition polymerisation of polymerisable olefinically unsaturated monomers. However, free radical initiation is preferred. Application of heat may assist the polymerisation although by suitable choice of catalyst it is possible to effect polymerisation at or near ambient temperature. Vinyl comonomers which may be used in admixture and with which the oligomers may be copolymerised include vinyl esters, aromatic vinyl compounds and vinyl nitriles.

Suitable vinyl esters include, for example, vinyl acetate and esters of acrylic and methacrylic acids, which esters may have one or more ester groups, e.g. methyl, cyclohexyl, n-hexyl, and tetrahydrofurfuryl acrylates and methacrylates, ethylene glycol acrylate and methacrylate, di- and triethylene glycol acrylates and methacrylates, and pentaerythritol triacrylate. As examples of suitable aromatic vinyl compounds may be mentioned inter alia styrene and derivatives thereof, e.g. alpha-methyl styrene, and vinyl toluene. Suitable vinyl nitrile compounds include inter alia acrylonitirle and derivatives thereof, e.g. methacrylonitrile.

Where a polymerisable olefinically unsaturated comonomer is present in the composition it typically provides between 5 and 95% by weight of the composition. The quantity of polymerisable olefinically unsaturated comonomer which is used will depend on inter alia the viscosity which is required and on the mechanical properties required in the cured resin prepared therefrom.

Compositions according to the first aspect of the present invention, particularly those which comprise an oligomer which has pendant and/or terminal acyloxymethyl groups in which the acyl group is derived from a polymerisable olefinically unsaturated carboxylic acid, are often highly resistant to aggressively corrosive environments, e.g. pH 12° at 80° C. for 24 hours and chromic acid at 60° C. for 30 minutes, and may find use in a variety of applications.

Such compositions when filled with one or more suitable particulate fillers, e.g. a borosilicate glass powder of silica powder, to a suitable level, typically 30–92% w/w of filler, have properties, e.g. low water uptake, low level of ionic impurities, high softening point, low shrinkage and good tracking resistance. They may be used as dental materials, for example as unfilled sealants, adhesives, bonding agents and glazes, or, where filled with a particulate filler, e.g. glass particles, as artificial teeth or dental fillings. They may be used in electronic or electrical applications, for example in photoresists, e.g. non-strippable dry film resists, in solder masks and, when filled, as encapsulants. They may be used in reprographic processes, e.g. in the preparation of printing plates. They may be used as abrasion resistant surface coatings, particularly when in admixture with a particulate filler.

Where compositions according to the first aspect of the present invention are used in or as dental materials, curing thereof is preferably effected by a visible light curing technique using a photo-initiator system, for example as disclosed in British Patent Specification No. 1408265, or preferably in European Patent Publication No. 59649A, the disclosure in which publication is incorporated herein by way of reference. Such compositions are particularly useful as the matrix in visible light cured radio-opaque dental filling materials. Where they are used in dental filling materials a copolymerisable comonomer may be present and the ratio of oligomer to comonomer may be chosen to give a refractive index equal to the refractive index of the filler, thus rendering the composition substantially transparent to the curing radiation and hence increasing the depth of cure. Where they are used in dental filling materials it will be appreciated that the weight ratios of oligomer:copolymerisable comonomer, where present:particulate filler is such that the material is a viscous fluid, that is paste-like and not powdery or crumbly at ambient temperatures, so that in the uncured state it may be shaped in a coherent mass and will maintain that shape without substantial flow; typically such weight ratios lie in the range 2-3:1-2:20-22. Such characteristics will enable the composition to be inserted into a substantially vertical cavity in or mould on a tooth in the upper jaw without deformation before cure.

Accordingly, a third aspect of the present invention provides a fluid dental filling material which comprises (a) at least one oligomer which is derived from an aromatic compound and an aldehyde and which has pendant and/or terminal acyl-oxymethyl groups in which the acyl group is derived from a polymerisable olefinically unsaturated carboxylic acid, which oligomer is preferably as defined in the first aspect of the present invention, and (b) a particulate filler.

The oligomer used in the third aspect of the present invention preferably has a functionality of between 2 and 5 and a number average molecular weight of between 500 and 1000.

Where a composition according to the first aspect of the present invention which comprises an oligomer in which the pendant and/or terminal groups comprise acyloxymethyl groups in which the acyl group is derived from an olefinically unsaturated carboxylic acid are used as reprographic materials, curing is effected by a photo curing technique, for example using the photo-initiator compositions described in our European Patent Publication No. 90493A, and a suitable low-powered laser beam, e.g. from an argon source. We have found that such compositions may be gelled in a few one-thousandths of a second and may be used as so called "camera speed resists". Such resists may be used in the production of printed circuits, letterpress printing plates (where the print is in relief) and lithographic printing plates (where the plate is essentially planar and has both oleophilic, ink receptive areas, and hydrophilic, ink-repellent areas). The oligomer used in such applications preferably has a functionality of at least four.

Accordingly a fourth aspect of the present invention provides a camera speed resist comprising (i) a polymerisable composition which comprises at least one oligomer which (a) is derived from an aromatic compound and an aldehyde and (b) has pendant and/or terminal acyloxy-methyl groups in which the acyl group is derived from a polymerisable olefinically unsaturated carboxylic acid, which oligomer is preferably as defined in the first aspect of the present invention, and (ii) a photoinitiator composition.

In an often preferred method of use, a camera speed resist of the fourth aspect of the present invention is typically coated on a conventional lithographic plate. The resist is then polymerised at those points where a permanent image is not required. The unpolymerised regions of the resist are dissolved in a suitable solvent to leave one or more exposed regions of the plate on which a metal, e.g. copper or nickel, is subsequently deposited, electrolytically or electrolessly. After deposition of the metal, the polymerised portions of the resist are removed.

Compositions according to the first aspect of the present invention comprising an oligomer which (a) has pendant and/or terminal groups which are acyloxymethyl groups in which the acyl group is derived from a polymerisable olefinically unsaturated carboxylic acid, and (b) has a functionality of at least three may be mixed with a photosensitive polymerisation initiator and formed into a cohesive tack-free film, either directly or, particularly where the number average molecular weight of the oligomer is less than 1000, after admixture therewith of a so-called polymeric binder as hereinbefore described. Such a film may be used as a so-called non-strippable or permanent dry film resist.

Accordingly a fifth aspect of the present invention provides a photopolymerisable composition which comprises (a) a polymerisable composition which comprises at least one oligomer which (i) is derived from an aromatic compound and an aldehyde and (ii) has pendant and/or terminal acyloxy methyl groups in which the acyl group is derived from an olefinically unsaturated carboxylic acid and has a functionality of at least three, which oligomer is preferably as defined in the first aspect of the present invention, and (b) a photo-sensitive initiator.

For use as a permanent dry film resist a photopolymerisable composition according to the fifth aspect of the present invention is firstly converted into a film. Conveniently the film is formed by casting from a solution in a suitable volatile solvent, e.g. methyl ethyl ketone. Typically the film is formed between a support film and a cover film to which the oligomer does not adhere and which do not soften or unduly disorientate, where orientation is present therein, during the film-forming process. Often the cover film is polyethylene and the support film is polyethylene terephthalate. Typically a permanent dry film resist formed from a photopolymerisable composition of the fifth aspect of the present invention has a thickness in the range 5 to 100 microns, although it will be appreciated that the thickness of the film will depend on the particular application for which it is to be used.

The cover film, typically a polyethylene film, is removed to expose one surface of the film of the photopolymerisable composition of the fifth aspect the present invention. The said exposed surface is brought into contact with a surface of a circuit board, e.g. a glass-fibre reinforced epoxy, on which the printed circuit is to be carried. The film is bonded to the circuit board, preferably by the application of mild heat and pressure thereto, although we do not exclude the possibility that a suitable bonding aid and/or adhesive may be employed.

Certain defined portion(s) of the film of the photopolymerisable composition of the fifth aspect of the present invention is/are subjected to suitable electromagnetic radiation, typically a radiation which is conventionally employed in manufacturing processes in the electronics industry, e.g. with a peak output in the range 300 to 500 nanometers, which initiates polymerisation of the photopolymerisable composition to form a film of cured resin. The support film is removed and then the unpolymerised portions of the photopolymerisable composition are removed to expose one or more portions of the circuit board. The circuit board is then subjected to further processing techniques, in which a conductive layer, e.g. copper is deposited on the said exposed portions, with no undue deleterious effect on the film of cured resin.

Where a solder mask comprises a composition according to the first aspect of the present invention it is preferably used in the form of a coherent tackfree or solid film, one surface of which is in contact with a suitable support film, and one surface of which is in contact with a cover film.

Polymerisable compositions according to the first aspect of the present invention in which the pendant and/or terminal groups on the oligomer are acyloxymethyl groups in which the acyl residue is derived from a saturated aliphatic carboxylic acid or an aromatic carboxylic acid and/or a substituted derivative thereof may be cured under suitable conditions to give resins having useful properties, e.g. glass transition temperatures in the range 80° C. to 290° C., depending on the functionality and molecular weight of the oligomer. Moreover, the resins may form the matrices for useful fibre-reinforced composites, particularly where the fibre is carbon fibre.

Accordingly, a sixth aspect of the present invention provides cured resins, and composites thereof, formed by curing a composition which comprises an oligomer which (a) is derived from an aromatic compound and an aldehyde and (b) has pendant and/or terminal acyloxymethyl groups in which the acyl group is derived from a saturated aliphatic carboxylic acid, or an aromatic carboxylic acid, or a substituted derivative thereof which oligomer is preferably as defined in the first aspect of the present invention.

Curing of an oligomer which has pendant and/or terminal groups which are acyloxymethyl groups the acyl group of which is derived from a saturated aliphatic carboxylic acid or an aromatic carboxylic acid or a substituted derivative thereof may be effected by heating the oligomer, typically up to about 80° to 140° C., preferably in the presence of a suitable catalyst, e.g. boron trifluoride etherate. Alternatively, particularly where the oligomer is in the form of a film or sheet, it may be irradiated with suitable electromagnetic radiation in the presence of a compound which interacts with the electromagnetic radiation to generate a cationic species which initiates curing of the oligomer (which compounds are hereinafter referred to for convenience as "photo sensitive cationic initiators") and hence causes curing thereof to form a cured resin.

Photo-sensitive cationic initiators are well known in the art, see for example Journal Macromolecular Science, Reviews in Macromolecular Chemistry, 1981-82, C21, pages 238-39. As examples thereof we would mention inter alia diaryl iodonium salts, e.g. diphenyl iodonium hexafluorophosphate and triaryl sulphonium salts, e.g. triphenyl sulphonium hexafluorophosphate. The less nucleophilic the anion the faster is the speed of polymerisation.

Oligomers of which a composition according to the first aspect of the present invention is comprised which have pendant and/or terminal carboxyl groups may be reacted with a suitable co-reactant, e.g. a bisepoxide or bisoxazoline, to form resins having useful properties. Alternatively, they may be converted into intermediates, e.g. oxazolines, by reaction with ethanolamine, which intermediates may be reacted with suitable co-reactants to form further useful resins. For example, the oxazolines may be reacted with dicarboxylic acids.

Oligomers of which a composition according to the first aspect of the present invention is comprised which have pendant and/or terminal hydroxymethyl groups can be cured by heating, for example to a temperature in the range 80° C. to 150° C. They have the advantage that no acid by-products are produced during the curing process.

Oligomers of which a composition according to the first aspect of the present invention is comprised which have pendant and/or terminal

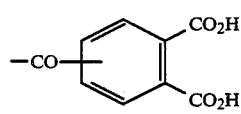

groups may be cured by reacting with, for example, a diamine to form a polyimide resin.

Oligomers of which a composition according to the first aspect of the present invention is comprised which have pendant and/or terminal

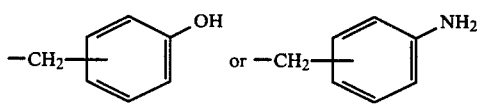

groups may be cured by reaction with, for example, a suitable formaldehyde-source, e.g. hexamethylene tetra-amine or, for the terminal amino oligomer, a suitable anhydride, e.g. pyromellitic anhydride.

Where compositions according to the present invention are used to provide the matrices for fibre-reinforced composites suitable fibre reinforcing materials include, for example, glass, e.g. in the form of mat, tapes, continuous fibre or chopped rovings, carbon fibre, inorganic mineral fibres and fibres of organic polymers, e.g. polyamides and polyesters.

Where a cured resin derived from a composition of the first aspect of the present invention is used as a matrix for a fibre-reinforced composite, such a composite may be produced for example by placing the fibres, for example carbon fibres, in a mould of the desired shape and then impregnating the fibres with the composition. The composition may then be allowed or caused to cure. Where the composition is a solid or is very viscous and is thus not sufficiently fluid for satisfactory impregnation of the fibres, the composition may be diluted with a low boiling solvent in order to provide a mixture of the desired fluidity, the low boiling solvent being caused or allowed to evaporate before the composition is cured.

Compositions according to the first aspect of the present invention may include inter alia heat and light stabilisers, antioxidants, colouring pigments and particulate filler materials, e.g. chalk, calcium carbonate, talc, mica, carbon black and glass.

Where curing of compositions according to the first aspect of the present invention is initiated by an initiator composition, particularly a photo-initiator composition, the concentration thereof in the composition may be in the range 0.01% to 10% by weight. For example, for permanent dry film resists the concentration of the photo-initiator composition in the composition may be in the range 1% to 4% by weight; for dental materials the concentration of the photo-initiator composition in the material may be in the range 0.1% to 1.0% by weight; and for camera speed resists the concentration of the photo-initiator composition may be in the range 0.1% to 2.0% by weight.

It will be appreciated that where photo-initiator compositions are used in the present invention that part of the preparation of photo-polymerisable compositions in which the photo-initiator composition is added, and subsequent manipulations, e.g. preparation of a film or paste, should be carried out in the substantial absence of the electro-magnetic radiation to which the photoinitiator composition is sensitive.

Whilst various additives, e.g. fillers, reinforcing materials or inert diluents, may be present in the compositions according to the present invention which comprise photo-initiator compositions it will be appreciated that where such additives are present they are such that they do not unduly diminish the transparency or translucency of the compositions. Where the transparency or translucency of the composition is unduly diminished polymerisation thereof may be reduced or prevented.

The invention is now illustrated by the following Examples.

In the Examples:

Number average and weight average molecular weights were determined by gel permeation chromatography on a Waters Liquid Chromatograph fitted with $\mu$ Styragel (Registered Trade Mark) columns;

Flexural properties were determined under the conditions of ASTM.

EXAMPLE 1

This example illustrates the preparation of an oligomer in which at least a portion of the functionality is provided by formyloxymethyl groups and which can be converted into an oligomer as defined in the first aspect of the present invention.

Distilled diphenyl oxide (340 grams; 2.0 moles), paraformaldehyde (280 grams; 9.3 moles), formic acid (1200 mls; 31.8 moles) and orthophosphoric acid (16 mls; 0.28 moles; specific gravity 1.75) were mixed, stirred and heated to 80° C. when a vigorous reaction occurred. When the reaction subsided, the resulting clear solution was refluxed for 6 hours and allowed to cool overnight.

A white solid separated out, the mother liquors were decanted and the solid was washed with water. It was dissolved in hot chloroform, the solution cooled, washed with saturated $NaHCO_3$ until free of acid, then with saturated NaCl and finally dried over $MgSO_4$. Emulsions which formed in the washing stages were broken by filtration through celite.

Most of the solvent was removed on a rotavapour leaving a viscous transparent liquid. This was further dried in a vacuum oven at 100° C. to leave a viscous liquid which on cooling set to a glassy solid of softening point 52° C. (hot-stage microscope) (Yield 380 grams). The glassy solid has a number average molecular weight of 1116 and a weight average molecular weight of 1403 (Mw/MN=1.26). The saponification value of the glassy solid was 170 mgs KOH/gram; the functionality thereof was 3.4; infra-red analysis indicated the presence of >C=O (1725 cm$^{-1}$), $\phi$—O—$\phi$ (1240 cm$^{-1}$) and C—O ester (1170 cm$^{-1}$); and proton magnetic resonance spectroscopy (in deuterochloroform) indicated the presence of carboxylic H (8 ppm; singlet), aromatic protons (7 ppm; multiplet), AR-$\underline{CH_2}$OCOH (5.2 ppm; multiplet) and O—$\phi$—CH$_2$—$\phi$— (3.9 ppm; singlet).

EXAMPLE 2

This example illustrates the preparation of an oligomer which can be converted into an oligomer as defined in the first aspect of the present invention.

The procedure of Example 1 was repeated except that 250 grams (8.3 moles) of paraformaldehyde were used instead of 280 grams and 25 mls (0.43 moles) of orthophosphoric acid were used instead of 16 mls.

The product was a glassy solid (Yield 445 grams) of trifluoroacetoxymethyl pendant and/or terminal groups and use of a portion of the carboxylic acid as the strong acid in the preparation thereof.

TABLE 1

| | Reaction Conditions | | | | | | | Product | | |
|---|---|---|---|---|---|---|---|---|---|---|
| Example | Diphenyl Oxide (moles) | Formaldehyde[a] (moles) | 85% Sulphuric Acid (mls) | Acetic Acid (mls) | Water (mls) | Time (Hours) | Yield (in grams) | $M_n$ | Number of Acetoxy Groups per Molecule[b] | Number of Hydroxy Groups per Molecule[c] | Functionality |
| 3 | 0.27 | 2.10 | 150 | 450 | 69 | 0.33 | 41 | 1324 | 4.2 | 1.7 | 5.9 |
| 4 | 0.17 | 0.70 | 50 | 150 | 23 | 0.5 | 32 | 1116 | 3.3 | 0.6 | 3.9 |
| 5 | 0.15 | 0.23 | 25 | 75 | 115 | 3 | [d] | 910 | 2.3 | 0.4 | 2.7 |
| 6 | 0.47 | 0.51 | 130 | 360 | 0 | 1 | 146 | 630 | 1.0 | 0.2 | 1.2 |
| 7 | 0.93 | 1.63 | 176 | 530 | 80 | 2 | 280 | 820 | 1.8 | 0.3 | 2.1 |
| 8 | 0.825 | 6.3 | 450 | 1350 | 270 | 0.33 | 98 | 1679 | 4.4 | 2.2 | 6.6 |
| 9 | 0.457 | 0.69 | 73 | 225 | 34.5 | 2 | 76 | 892 | 3.3 | 0.3 | 3.6 |
| 10 | 0.825 | 6.3 | 450 | 1350 | 2.70 | 0.33 | 176 | 1101 | 4.7 | 0.5 | 5.2 |
| 11 | 0.453 | 0.69 | 73 | 225 | 34.5 | 2 | 96 | 919 | 3.8 | d | d |
| 12 | 0.23 | 0.304[e] | 2 | 5 | | 2 | 46 | 975 | 2.5 | d | d |

[a]Used in the form of paraformaldehyde
[b]Determined by hydrolysis of the acetoxy groups with 0.5 M potassium hydroxide in 2-methoxy-ethanol
[c]Determined by acetylation with acetic anydride/acetic acid solution
[d]Not determined
[e]37% formaldehyde softening point 60° C. The product had a number average molecular weight of 1519 and a weight average molecular weight of 2432 (Mw/MN=1.52) and the functionality was found to be 4.2.

EXAMPLES 3–12

These examples (except Example 12) illustrate the preparation of oligomers as defined in the first aspect of the invention in which at least a portion of the functionality is provided by acetoxymethyl groups.

General Procedure

Acetic acid, water and 85% w/w sulphuric acid were added to paraformaldehyde and stirred to form a homogeneous solution which was heated to 78° C. Molten diphenyl oxide was added dropwise over several minutes to the hot solution whilst the temperature thereof was kept below 80° C. The reaction mixture was stirred at 78° C. and a white cloudy emulsion and/or a slurry formed. The hot reaction mixture was poured into a mixture of cold water (2 liters) and methylene chloride (500 mls). The resulting mixture was stirred for 15 minutes, the layers were allowed to separate, the aqueous layer was decanted off and the organic layer was washed with 10% bicarbonate solution and then with water until neutral. The organic layer was dried overnight over magnesium sulphate and the methylene chloride was evaporated on a rotary evaporator to leave a clear pale yellow viscous gum or a pale yellow brittle solid.

The reaction conditions and the characteristics of the products are given in Table 1. Proton magnetic resonance and infra-red spectroscopy confirmed the structures of the oligomers.

EXAMPLE 13

This example illustrates an oligomer as defined in the first aspect of the present invention in which there are Trioxan (8 grams; 267 milimoles) was added to a stirred solution of diphenyl oxide (11.34 grams; 67 milimoles), trifluoroacetic acid (51 mls; 667 milimoles) and trifluoroacetic anhydride (9.4 mls; 67 milimoles) in dichloromethane (250 mls; 3.17 moles). The reaction mixture was refluxed for 30 minutes under nitrogen then poured into sodium bicarbonate solution. The product was extracted into chloroform and recovered from the chloroform by dropwise addition of methanol.

The product (8.0 grams) was found by GPC, to have Mn of 6800, and Mw of 18,829. DSC indicated a softening point of 152° C. and quantitative $C^{13}$ nuclear magnetic resonance spectroscopy indicated that the ratio of parapara to ortho-para linkages was 2:1.

EXAMPLES 14–16

These examples illustrate oligomers as defined in the first aspect of the present invention which have methacryloyloxymethyl pendant and/or terminal groups.

Diphenyl oxide was added over 1–2 minutes to a clear solution of 98% sulphuric acid, water, paraformaldehyde and methacrylic acid (containing 100 ppm hydroquinone and 100 ppm Topanol O) at 60° C. The reaction mixture was well stirred and the temperature thereof was maintained at 60°–75° C.

After 1.25 hours, less than 1% of the diphenyl ether was unreacted, as shown by GLC. The reaction mixture was allowed to separate into two layers, the upper organic layer was recovered and Topanol (2 grams) was added thereto. The organic layer was washed with hot (60° C.) water (3×8 liters) and a viscous white liquid was obtained. The liquid was dissolved in methylene chloride, the resulting solution was washed with saturated sodium bicarbonate solution, dried over magnesium sulphate and the solvent was removed on a rotavapour to leave a pale yellow viscous liquid.

TABLE 2

| Example No. | Reaction Conditions | | | | | | Product | | | | | | |
|---|---|---|---|---|---|---|---|---|---|---|---|---|---|
| | Diphenyl Oxide (moles) | Formaldehyde[a] (moles) | Sulphuric Acid[b] (moles) | Water (moles) | Methacrylic Acid (moles) | Reaction Temperature (°C.) | Yield (Kilograms) | $M_n$ | $M_w$ | $M_w/M_n$ | Number of Methacryloxy Groups per molecule | Number of Hydroxy Groups per Molecule | Topanol Concentration (ppm) |
| 14 | 7.18 | 56 | 58.9 | 160 | 94 | 63 | 1.9 | 882 | 1348 | 1.53 | 4.20 | 0.60 | 1066 |
| 15 | 6.04 | 9.3 | 45.1 | 122 | 58.7 | 68 | 1.1 | 707 | 960 | 1.36 | 1.72 | 0.19 | 690 |
| 16 | 7.18 | 66.7 | 58.9 | 160 | 94 | 75 | 2.1 | 988 | 1395 | 1.40 | 4.95 | 0.84 | 590 |

[a] As paraformaldehyde
[b] 98%

Details of the reaction conditions and products are given in Table 2.

Quantitative $C^{13}$ nuclear magnetic resonance spectroscopy indicated that in Examples 14 and 16 the ratios of para-para linkages to ortho-para linkages were 3.4:1 and 3.8:1 respectively.

EXAMPLE 17

This example illustrates an oligomer as defined in the first aspect of the present invention derived from diphenyl and diphenyl oxide.

A warm solution of diphenyl (3.5 grams; 22.5 milimoles) and diphenyl oxide (5.8 grams; 22.5 milimoles) in acetic acid (7.5 mls) was added to a solution of paraformaldehyde (5.4 grams; 180 milimoles) in acetic acid (30 mls) and 98% sulphuric acid (12 mls) at 75° C. After 10 minutes stirring at 75° C., a sticky solid separated from the reaction mixture, and water and then methylene chloride were added to the reaction mixture. The oligomer was recovered from the methylene chloride as a pale yellow solid (7 grams), Mn 857, (Mw/Mn) 2.5, softening point 70°-115° C., functionality 1.5 acetoxymethyl groups.

EXAMPLES 18 and 19

These examples illustrate oligomers as defined in the first aspect of the present invention derived from diphenyl.

Diphenyl was added to a solution of paraformaldehyde in acetic acid (25 mls) and 98% sulphuric acid (8 mls) at 90° C. A solid rapidly separated from the reaction and within 5 minutes the reaction mixture was in the form of a yellow sticky solid. Water and then methylene chloride were added to the reaction mixture and the oligomer was recovered from the methylene chloride.

The results are shown in Table 3.

TABLE 3

| Example No | Diphenyl (moles) | Formaldehyde (moles) | $M_n$ | Number of Acetoxy Groups per Molecule |
|---|---|---|---|---|
| 18 | 0.03 | 0.24 | 586 | 1.7 |
| 19 | 0.06 | 0.24 | 525 | 0.7 |

EXAMPLE 20

This example illustrates an oligomer as defined in the first aspect of the present invention derived from diphenyl and having dichloroacetoxymethyl pendant and/or terminal groups.

Dichloroacetic acid (6.2 grams), followed by 85% w/w sulphuric acid (30 grams), was added with stirring to a mixture of diphenyl (1.0 grams; 6.5 milimoles) and 37% formaldehyde solution (1.1 gram; 13.6 milimoles) stirred at 45° C. A clear solution formed, within 3 minutes a product began to separate, and stirring was continued for 15 minutes. The reaction was cooled, water (100 mls) was added, the product was filtered, washed with water (3x) and dried at 50° C. for 18 hours at 1.0 mm Hg. The oligomer (1.1 gram) was obtained as a pale brown solid, softening point 120°-160° C. GPC examination of the solid indicated $M_n=868$, $M_w=1094$ and less than 2% of unreacted diphenyl.

EXAMPLE 21

This example illustrates an oligomer as defined in the first aspect of the present invention derived from naphthalene and having dichloroacetoxymethyl pendant and/or terminal groups.

Dichloroacetic acid (6 grams), followed by 85% sulphuric acid (3.0 grams), was added with stirring to a mixture of naphthalene (1.0 gram; 7.8 milimoles) and 37% formaldehyde solution (2.0 grams; 24.7 milimoles) at 50° C. The resulting turbid mixture was stirred at 50° C. for 35 minutes and then worked up as in Example 20. The oligomer (1.1 grams) was obtained as a pale yellow solid with softening point of 80°-120° C. GPC examination of the solid indicated $M_n=985$, $M_w=1253$ and no detectable naphthalene.

EXAMPLE 22

This example illustrates an oligomer as defined in the first aspect of the present invention derived from p,p'-diphenoxydi-phenyl sulphone.

A mixture of paraformaldehyde (0.10 grams), glacial acetic acid (3 mls) and 85% sulphuric acid (4.5 grams) was heated at 70° C. until a clear solution was obtained. A solution of p,p'-diphenoxy-diphenyl sulphone (1.3 grams) in warm 1,2-dichloroethane (3 mls) was added to the solution. The reaction mixture was stirred at 65° C. for 5.5 hours. Two separate liquid phases formed, which were cooled and distilled water (20 mls) added thereto. The organic material was extracted into methylene chloride and the oligomer recovered therefrom as a white powder (1.2 grams) of softening point 150° C., $M_n$997 and $M_w$1389.

EXAMPLE 23

This example illustrates an oligomer as defined in the first aspect of the present invention derived from p,p'-diphenoxy-benzophenone.

A solution of p,p'-diphenoxybenzophenone (1.1 grams) in 1,2-dichloroethane (6 mls) was added to a homogeneous mixture of paraformaldehyde (0.11 grams), glacial acetic acid (3.0 mls) and 85% sulphuric acid (4.2 grams) at 65° C. A clear solution was obtained which was stirred at 65° C. After 3 hours, the reaction mixture was heterogeneous and its viscosity had increased. After 9 hours, the reaction mixture was cooled, diluted with water and extracted with methylene chloride. The oligomer was obtained as a dark brown solid (1.1 grams) of $M_n$ 1120 and $M_w$ 1506. containing about 3% of unreacted p,p'-diphenoxybenzophenone.

EXAMPLES 24–27

Examples 25 and 27 illustrate the preparation of oligomers as defined in the first aspect of the present invention having hydroxymethyl pendant and/or terminal groups.

General Procedure

Oligomers having functionality provided by formoxymethyl or acetoxymethyl groups, potassium hydroxide, and 2-methoxyethanol were refluxed to form a brown solution which was allowed to cool and then poured into cold water (2 liters) when a pale yellow solid precipitated. This was filtered and the resulting "tacky" solid washed thoroughly with water, it was then pumped dry in a vacuum-oven at 60° C. and the resultant cake ground in a mortar and pestle. The ground solid was added to methanol (2 liters) with stirring and a sticky solid formed. This was filtered, pumped partially dry in a vacuum-oven, ground and dried in a vacuum-desiccator over silica gel to give a pale cream solid.

Infra-red analyses of the products indicated the presence of —OH groups (broad absorbance at 3380 cm$^1$) and the absence of ester and carbonyl groups; and proton magnetic resonance spectroscopy indicated the presence of aromatic protons (7 ppm; multiplet), —CH$_2$OH (4.6 ppm; broad doublet), —φ—CH$_2$—φ— (3.9 ppm; singlet) and hydroxyl (2.8 ppm; broad singlet which disappears on shaking with D$_2$O). Other characteristics of the products, and the reaction conditions employed for the preparation thereof are given in Table 4.

EXAMPLES 28–31

These examples illustrate oligomers as defined in the first aspect of the present invention having carboxyl pendant and/or terminal groups.

General Procedure

Jones reagent (prepared from chromic acid (85 grams), water (248 mls) and concentrated sulphuric acid (72 mls)) was added slowly with stiring to an acetone suspension of oligomer in which the functionality is provided by hydroxymethyl groups. A vigorous reaction ensued the acetone refluxed and a thick green solid precipitated out of solution. The mixture was stirred and refluxed for 1.5 hours and then cooled to ambient temperature.

A yellow brown solution separated out above a green oily layer. The solution was decanted, concentrated to approximately 1 liter and then poured into approximately 3 liters of water with stirring. A pale cream solid precipitated, which was filtered, washed with water and dried in a vacuum-oven at 80° C. and then in a vacuum-desiccator over silica gel to give a pale cream solid. Infra-red analysis indicated the presence of OH (3200 cm$^{-1}$; broad) and carbonyl (1690 cm$^{-1}$) and proton magnetic resonance (in D6-acetone) indicated the presence of

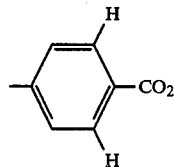

TABLE 4

| | Reaction Conditions | | | | Product | | | |
|---|---|---|---|---|---|---|---|---|
| Example | Precursor Prepared in Example | Weight of Precursor (grams) | Wt of KOH (grams) | Reflux Time (hours) | Yield (grams) | $M_n$ | Functionality[a] | Softening Point[b] (°C.) |
| 24 | 1 | 220 | 50 | 1 | 180 | 1126 | 3.6 | 80 |
| 25 | 2 | 400 | 103 | 2 | 310 | 1473 | 4.2 | 92 |
| 26 | 7 | 126 | 16 | 1 | 104 | 743 | 2.4 | 55 |
| 27 | 8 | 77 | 13 | 1 | 66 | 1494 | 6.7 | 85 |

[a]Determined by acetylation with acetic anhydrode/acetic acid solution
[b]Determined on a hot-stage microscope (8.0 ppm; broad doublet), aromatic protons (7.0 ppm; broad multiplet) and —φ—CH$_2$—φ— (3.9 ppm; singlet).

Details of the reaction conditions and further characteristics of the products are given in Table 5.

EXAMPLES 32–38

These examples illustrate oligomers as defined in the first aspect of the present invention having carboxyl pendant and/or terminal groups and in-chain keto groups.

General Procedure

Oligomer (10 grams) was dissolved in pyridine (500 mls) and water (250 mls) was added with stiring; partial precipitation of the oligomer with formation of an emulsion occurred. Potassium hydroxide (10 grams) and potassium permangamate (25 grams) were added to the emulsion and the mixture was stirred at 80° C. for 8 hours. Equal weights of potassium hydroxide and potassium permangamate were added, where required, during the reaction to maintain the pH of the reaction mixture above 7 and the colour thereof purple. Water (250 ml) was added to the reaction and the reaction mixture was filtered. The solid residue was washed with dilute potassium hydroxide solution and then several times with water. The combined washings and filtrate were acidified with hydrochloric acid, and a white solid was precipitated which was filtered, washed thoroughly with water and dried under vacuum at 60° C.

Traces of pyridine associated with the products were removed by converting the carboxyl groups of the products into sodium salts, and azeotroping with water until no pyridine was detected in the distillate (by UV). The free acids were regenerated and dried.

TABLE 5

| | Reaction Conditions | | | | | Product | | | |
|---|---|---|---|---|---|---|---|---|---|
| Example | Precursor Prepared in Example | Weight of Precursor (gms) | Jones Reagent (mls) | Temperature (°C.) | Time (hrs) | Yield (gms) | $M_n$ | Functionality[a] | Equivalent Weight[b] | Softening Point[c] (°C.) |
| 28 | 24 | 100 | 150 | 20 | 16 | 46.8 | 1170 | 3.6 | 326 | 135 |
| 29 | 25 | 100 | 320 | 50 | 1.5 | 52.5 | 1532 | 4.3 | 358 | 145 |
| 30 | 26 | 50 | 105 | 20 | 16 | 34.2 | 760 | 1.7 | 447 | 78 |
| 31 | 27 | 60 | 240 | 50 | 1 | 38.2 | 1587 | 6.4 | 248 | 175 |

[a]Determined by titration against alcoholic potassium hydroxide
[b]Equivalent weight = $\frac{M_n}{\text{Functionality}}$
[c]Determined on a hot-stage microscope Infra-red analyses of the products indicated the presence of carboxyl groups (1690 cm$^{-1}$) and in-chain keto groups (1640 cm$^{-1}$) and the absence of ester groups (no absorption at 1730 cm$^{-1}$). Proton magnetic resonance analyses of the products indicated the presence of aromatic protons (0–10 ppm) and the absence of aliphatic protons.

The products are generally soluble in tetrahydrofuran, dioxan, methoxyethanol, dimethyl sulphoxide and pyridine and generally insoluble in chloroform, methylene chloride, toluene and acetone.

Details of the products are given in Table 6. Yields can be improved by using sulphur dioxide instead of hydrochloric acid in the neutralisation step.

TABLE 6

| Example | Precursor Prepared in Example | Yield (%) | Equivalent Weight | Softening Point[a] (°C.) |
|---|---|---|---|---|
| 32 | 6 | 50 | 876 | 75 |
| 33 | 5 | 55 | 322 | 107 |
| 34 | 4 | 60 | 239 | 115 |
| 35 | 3 | 30 | 252 | 121 |
| 36 | 1 | 85 | 358 | 110 |
| 37 | 7 | 70 | 320 | b |
| 38 | 8 | 55 | 321 | b |

[a]Determined by differential scanning calorimetry
[b]Not determined

EXAMPLE 39

This example illustrates an oligomer as defined in the first aspect of the present invention in which phenolic pendant and/or terminal groups are present.

A sample (1.55 grams) of the resin prepared in Example 12, phenol (0.304 grams) and p-toluene-sulphonic acid (0.052 grams) were heated at 65° C. for 3 hours. A clear mobile melt was obtained and acetic acid was evolved. Vacuum was slowly applied to the melt and its temperature was raised to 80° C. After a total reaction time of 4.5 hours the melt was cooled, and a glassy pink solid formed which was dissolved in 3N caustic soda solution (15 mls). The solution was filtered, and acidified with hydrochloric acid. The precipitate which formed was extracted into chloroform. The chloroform solution was washed with water until neutral, dried over sodium sulphate and evaporated at 50° C. under vacuum. The oligomer was obtained as a solid (1.3 grams), softening point 50°–110° C. and Mn 1040. No free phenol was detected by GPC and no carbonyl groups were detected by infra-red spectroscopy.

EXAMPLE 40

This example illustrates an oligomer as defined in the first aspect of the present invention in which amino pendant and/or terminal groups are present.

A sample (7.3 grams) of the hydroxymethyl oligomer prepared in Example 24 and aniline (10 mls) were heated to 90° C. under nitrogen. 45% Boron trifluoride etherate (0.2 mls) was added and the reaction mixture was heated to 170° C. After 5 hours, proton magnetic resonance spectroscopy indicated the absence of hydroxymethyl groups. The reaction mixture was cooled, methanol (100 mls) was added and the product precipitated. The oligomer (7.8 grams) had a softening point of 90° C., $M_n$ 1096, $M_w$ 1462.

EXAMPLES 41–43

These examples illustrate cured resins according to the sixth aspect of the present invention derived from oligomers having acetoxymethyl pendant and/or terminal groups.

Boron trifluoride etherate was added to a solution of oligomer in chloroform or methylene chloride. The chloroform was removed under vacuum at 40° C. and a sample of the residue was cured at 140° C., and 20,000 psi for 30 minutes to give resins in the form of plaques. The mechanical properties of the resins are shown in Table 7.

TABLE 7

| | Oligomer | | | Weight | | | |
|---|---|---|---|---|---|---|---|
| Example No | Source Example No | Solvent | Weight (grams) | of Catalyst (grams) | Flexural Modulus GN/m$^2$ | Flexural Strength MN/m$^2$ | Softening Point (°C.) |
| 41 | 10 | CHCl$_3$ | 50 | 0.37 | 2.6 | 87 | 75[b] |
| 42 | 11 | CHCl$_3$ | 10 | 0.10 | 2.2 | 82 | a |
| 43 | 17 | CH$_2$Cl$_2$ | 2 | 0.02 | a | a | 120[cd] |

[a]Not determined
[b]By TMA
[c]By DMA
[d]Post-cured at 80° C. for 24 hours and 150° C. for 16 hours.

EXAMPLES 44–45

These examples illustrate cured resins according to the sixth aspect of the present invention derived from oligomers having methacrylyloxymethyl pendant and-/or terminal groups.

A portion (10 grams) of the oligomer prepared in Example 14 was warmed to 50° C. and catalyst (0.1 gram) was added. Samples of the mixture were cured at:
A. 85° C. for 18 hours,
B. 85° C. for 18 hours then 140° C. for 18 hours.

The mechanical properties of the cured samples are shown in Table 8.

TABLE 8

| Example No. | Catalyst | Cure Cycle A | | Cure Cycle B | |
|---|---|---|---|---|---|
| | | Flexural Strength MPa | Flexural Modulus GPa | Flexural Strength MPa | Flexural Modulus GPa |
| 44 | Benzoyl peroxide | 62.5 | 2.93 | 121 | 3.90 |
| 45 | t-Butyl per (2-ethyl) hexanoate | 98.5 | 3.41 | 120 | 3.73 |

EXAMPLES 46-59

These examples illustrate the preparation of cured resins from oligomers as defined in the first aspect of the present invention.

Mixtures of oligomers as defined in the first aspect of the present invention in which the functionality is provded by carboxyl groups and epoxy resins of bis-phenol-A-epichlorohydrin (Epikote (RTM), ex Shell Chemicals) were prepared as follows:

Heat Mixing

Oligomer and epoxy resin containing equivalent amounts of carboxyl groups and epoxy groups (except where indicated) were heated together at about 170° C. for 5-10 minutes and stirred with a spatula. The components were well mixed. The mixture was cooled and the resulting solid was ground to a powder.

Solution Mixing

Oligomer and epoxy resin containing equivalent amounts of carboxyl groups and epoxy groups were dissolved in tetrahydrofuran to give a clear solution. The tetrahydrofuran was removed by vacuum distillation and the resulting powdery foam was dried overnight at about 75° C. under high vac.

The mixtures were moulded at 120°-180° C. for 5-30 minutes at 1000 psi.

The moulded samples were cured in four stages, each of four hours, at 125° C., 150° C. 175° C. and 200° C.

Details of the reagents used and the properties, softening points and dynamic mechanical analyses, of the products are given in Table 9.

TABLE 9

| | | | Product | | | | | |
|---|---|---|---|---|---|---|---|---|
| Example | Oligomer Prepared in Example | Epikote Reference Number | Glass Transition Temperature$^d$ | Young's Modulus (GPa) | | | Flexural Tests | |
| | | | | −50° C. | 20° C. | 100° C. | Modulus (GPa) | Strength (MPa) |
| 46 | 37 | 828 | 144 | 2.7 | 2.3 | 2.0 | 2.1 | 46 |
| 47 | 38 | 1007 | 115 | 2.0 | 1.6 | 1.3 | 2.3 | 83 |
| 48 | 38 | 828 | 166 | 3.2 | 2.6 | 2.3 | 2.2 | 54 |
| 49 | 38 | 1007 | 113 | 2.3 | 1.8 | 1.5 | 2.0 | 43 |
| 50 | 38$^b$ | 828 | 146 | 3.2 | 2.8 | 2.2 | 2.5 | 73 |
| 51 | 38$^c$ | 828 | 162 | 3.2 | 2.8 | 2.3 | 2.2 | 64 |
| 52 | 38$^a$ | 828 | 170 | 2.4 | 2.0 | 1.6 | 2.5 | 80 |
| 53 | 34 | 1004 | 120 | 3.7 | 3.0 | 2.5 | 2.4 | 78 |
| 54 | 34 | 828 | 170 | 3.2 | 2.8 | 2.3 | 2.9 | 110 |
| 55 | 30 | 828 | 100 | 2.5 | 2.2 | 0.2 | 2.8 | 79 |
| 56 | 30 | 1007 | 110 | 2.9 | 2.4 | 1.6 | 2.3 | 80 |
| 57 | 31 | 828 | 206 | 2.9 | 2.5 | 2.1 | 2.5 | 50 |
| 58 | 31 | 1007 | 124 | 2.5 | 2.0 | 1.6 | 2.3 | 75 |
| 59 | 28 | 1004 | 150 | 2.7 | 2.4 | 1.9 | 2.9 | 105 |

$^a$Mixture was prepared by solution mixing; mixtures of the other Examples were prepared by heat mixing
$^b$Half the molar equivalent of acid was used
$^c$Three-quarters of the molar equivalent of acid was used
$^d$Determined by DMA.

We found that the carboxyl-functionalised oligomers in which there were methylene groups in the polymer backbone gave better mixtures with epoxy resins that the equivalent oligomers in which keto groups were present in the backbone.

EXAMPLES 60-66

These examples illustrate the preparation of cured resins from oligomers as defined in the first aspect of the present invention.

Equivalent amounts of oligomers as defined in the first aspect of the present invention in which the functionality is provided by carboxyl groups and m-phenylenebis(2-oxazoline) or p-phenylenebis(2-oxazoline) or an equimolar mixture thereof were ground together in a micro-mill for 2 hours. (The m-phenylenebis(2-oxazoline) and the p-phenylenebis(2-oxazoline) and the p-phenylenebis(2-oxazoline) were prepared by dehydration with oleum of N,N'-bis(2-hydroxyethyl)isophthalamide and N,N-bis(2-hydroxyethyl)-terephthalamide respectively as described in United Kingdom Patent Specification No. 1,468,874). The resulting powder was pressed in a 6×1 cm piston mould between sheets of Melinex at a temperature of 150°-190° C. and a pressure of about 1000 psi for upto 1 hour.

The clear brown moulding produced was cured further in a vacuum oven at 90° C. for 1-2 hours, followed by further heating at atmospheric pressure and temperatures up to 190° C. for 2 hours. Infra-red analysis of the product indicated the presence of ester (1710 cm$^{-1}$) and amide (1650 and 1540 cm$^{-1}$) linkages.

Details of the reactants and products are given in Table 10.

TABLE 10

| | | | | Reaction Conditions | | | | | Product | | | | |
|---|---|---|---|---|---|---|---|---|---|---|---|---|---|
| | | | | | Press Conditions | | Post-Curing Conditions | | Dynamic Mechanical Analysis | | | | |
| | Oligomer Prepared | | Weight Ratio of Oligomer to | Temp- erature | Time | Temp- erature | Time | Glass Transition Temper- | $E_{20}^a$ | $E_{100}^b$ | Flexural Properties | |
| Example | in Example | Oxazoline | Oxazoline | (°C.) | (hour) | (°C.) | (hour) | ature (°C.) | GPa | MPa | Modulus MPa | Strength GPa |
| 60 | 28 | A | 3.0 | 130 | 0.5 | 80 | 2 | 172 | 2.96 | 2.65 | 3.8 | 109 |
| | | | | | | 170 | 4 | | | | | |
| | | | | | | 190 | 2 | | | | | |
| 61 | 28 | C | 3.0 | 130 | 0.5 | 80 | 2 | 165 | 2.4 | 2.1 | 3.2 | 82 |
| | | | | | | 170 | 2 | | | | | |
| 62 | 28 | B | 3.0 | 130 | 0.5 | 100 | 1 | 172 | 2.32 | 2.15 | 2.9 | 95 |
| | | | | | | 170 | 2 | | | | | |
| 63 | 30 | A | 4.1 | 180 | 1 | 100 | 1 | 120 | 2.1 | 1.04 | 3.1 | 46 |
| | | | | | | 190 | 4 | | | | | |
| 64 | 31 | A | 2.3 | 180 | 0.5 | 100 | 1 | 158 | 2.7 | 2.35 | 3.2 | 85 |
| | | | | | | 170 | 4 | | | | | |
| 65 | 36 | A | 3.0 | 180 | 0.5 | 80 | 2 | 150 | 2.73 | 2.18 | 3.0 | 58 |
| | | | | | | 190 | 2 | | | | | |
| 66 | 29 | A | 3.3 | 195 | 1 | 90 | 1 | 165 | 3.23 | 2.85 | 3.2 | 83 |
| | | | | | | 180 | 2 | | | | | |
| CT | | | | | | 200 | 2 | 125 | 1.86 | 1.37 | 3.0 | 130 |

CT: Comparative test
A: phenylene bis(2-oxazoline)
B: phenylene bis(2-oxazoline)
C: A mixture of A and B in ratio of 1:1
$^a$Young's modulus at 20° C.
$^b$Young's modulus at 100° C.

In a comparative test an epoxy resin, Epikote EP 1001 (RTM; ex Shell Chemicals) (10 grams) and phthalic anhydride (3 grams) were mixed at 130° C., cast to form a plaque which was then post-cured. The properties of the product are shown in Table 10.

From Table 10 it can be seen that the resins of the present invention have a higher softening point and maintain their strength at higher temperatures than a commercially available resin.

EXAMPLE 67

This example illustrates the preparation of composites from oligomers as defined in the first aspect of the present invention.

Boron trifluoride etherate (700 microliters) was added with stirring to a portion (130 mls) of a solution prepared by dissolving a portion (72 grams) of the resin prepared in Example 9 in dry chloroform (240 mls). Carbon fibre was immersed in the mixture, removed therefrom and dried in a current of warm filtered air for 5 minutes. This was repeated until the carbon fibre was coated with an equal weight of the catalyst/oligomer mixture to form a so-called "pre-preg". The pre-preg were dried under a vacuum of 0.1 mm Hg for 18 hours at room temperature.

Layers of the pre-pregs were laid in parallel in a mould and cured at 140° C. and 20,000 psig for 1 hour, and then post-cured at 104° C. for 18 hours. The mechanical properties of the post-cured composites were determined in transverse flexural tests and short beam shear tests. The results are shown in Table 11.

EXAMPLE 68

This example illustrates a dental composition according to the present invention.

TABLE 11

| Transverse Flexural Test (Strength Values) MPa | | Short Beam Shear Test (Strength Values) MPa | |
|---|---|---|---|
| After storing | | | |
| 24 hours at room temperature. | After 24 hours in boiling water | After storing 24 hours at room temperature | After 36 hours in boiling water. |
| 46 | 40 | 54 | 41 |

A portion (25.68 grams) of the oligomer prepared in Example 14, barium borosilicate glass (Raysorb T3000, ex Owens, Ill.; 74.0 grams), camphorquinone (195 mgs) and N,N-dimethylaminoethyl methacrylate (130 mgms) were thoroughly mixed to give a composition which had a consistency typical of a dental composite.

A sample of the composition was polymerised by exposure to light of peak intensity at 470 nanometers and output 1000 watts/meters$^2$ (at 470±10 nanometers) for 60 seconds.

The polymerised product had a flexural strength of 75.3±7.4 MPa and a flexural modulus of 8.07 GPa.

EXAMPLE 69

This example illustrates a dental composition according to the present invention.

A portion (9.72 grams) of the oligomer prepared in Example 14, triethyleneglycol dimethacrylate (SR 205, ex Ancomer Chemicals; 6.08 grams), barium borosilicate glass (as described in Example 68; 84.0 grams), camphorquinone (120 mgms) and N,N-dimethylaminoethyl methacrylate (80 mgms) were thoroughly mixed to give a composition which had a consistency typical of a dental composite. The ratio of oligomer to triethylene glycol dimethacrylate was such that the organic component of the composition had a refractive index of 1.553, which was the same as that of the glass.

A sample of the composition was polymerised under the conditions described in Example 68.

The polymerised product had a flexural strength of 97.6±13.0 MPa and a flexural modulus of 16.44±1.16 GPa.

EXAMPLE 70

This example illustrates an oligomer as defined in the first aspect of the present invention having methacrylyloxymethyl pendant and/or terminal groups.

The procedure described in Example 14 was repeated except that 28 moles of paraformaldehyde were used instead of 56 moles.

Gel permeation chromatography revealed that oligomer had a $M_n$ of 763 and a $M_w$ of 1127.

The number of methacrylyloxy groups per molecule of oligomer was found to be 2.87 and the number of hydroxy groups per molecule of oligomer was found to be 0.45.

Quantitative $C^{13}$ nuclear magnetic resonance spectroscopy indicated that the ratio of para-para linkages to ortho-para linkages was 4.7:1.

EXAMPLE 71

This example illustrates an oligomer useful as a permanent dry film resist according to the present invention.

The general procedure described in Examples 3–12 was repeated using paraformaldehyde (10.5 grams; 0.35 moles), diphenyl oxide (24.4 mls; 0.15 moles), water (11.5 mls), glacial acetic acid (75 mls) and 85% sulphuric acid (25 mls), and the reaction was carried out for 2 hours at 78° C.

The product had a $M_n$ of 1150, a $(M_w/M_n)$ of 1.5, and a functionality of 4.4 (number of acetoxy groups per molecule=3.1; number of hydroxy groups per molecule=1.3).

EXAMPLE 72

This example illustrates an oligomer as defined in the first aspect of the present invention which has acrylyloxymethyl pendant and/or terminal groups.

A mixture of distilled water (28.8 grams; 1.6 moles), 98% sulphuric acid (58.9 grams; 0.6 moles) and paraformaldehyde (8.4 grams; 0.26 moles) was stirred and heated at 70° C. until a clear solution formed. Acrylic acid (84 grams; 1.17 moles), containing p-methoxyphenol (0.07 grams; 830 ppm based on acrylic acid) was added to the clear solution and the temperature was adjusted to 65° C., diphenyl oxide (12.2 grams; 0.072 moles) was then added over a period of 5 minutes while the temperature was kept below 70° C. The reaction mixture rapidly became opaque.

After a total reaction time of 30 minutes the reaction mixture was poured, with stirring, into cold distilled water (300 cc). The mixture was allowed to settle, the supernatant aqueous layer was decanted and the crude oligomer was washed with water (200 cc×2), and then dissolved in methylene chloride. The methylene chloride solution was washed repeatedly with water, dried over a molecular sieve and the solvent was removed under vacuum at 40° C. The oligomer was obtained as a semi-solid (12.8 grams); gel permeation chromatography indicated $M_n=932$, and $M_w=1198$; and the functionality was 3.4.

EXAMPLE 73

This Example is a comparative example which illustrates an oligomer known in the art.

Example 40 of U.S. Pat. No. 3,914,194 was repeated. Diphenyl oxide (8.5 grams), paraformaldehyde (4.47 grams), methacrylic acid (18.9 cc), p-toluene-sulphonic acid (0.95 grams) and p-methoxyphenol (0.6 grams) were heated at reflux for 90 minutes. To avoid polymerisation of methacrylic acid, it was found necessary to add further amounts (0.01 grams×3) of p-methoxyphenol during the reaction. The reaction mixture was poured into water (150 cc), and an oil was decanted and washed with warm water, dilute ammonia solution, and warm water (2x). The sticky viscous liquid which was obtained was dissolved in methylene chloride, dried over a molecular sieve, filtered and stipped at 50° C. under vac.

A pale straw viscous liquid (10.8 grams) was obtained; gel permeation chromatography indicated $M_n=1160$ and $M_w=1929$; quantitative $C^{13}$-nuclear magnetic resonance spectroscopy indicated that the ratio of para-para linkages to ortho-para linkages was 6.3:1.

A sample of the product, containing 2% w/w N,N-dimethyl-2-aminoethyl methacrylate and 1% w/w camphorquinone cured in daylight in approximately 5 minutes and was still soft and flexible after 24 hours. Under the same curing conditions a sample of the oligomer prepared in Example 14 cured in less than 30 seconds and was hard and rigid after 24 hours.

EXAMPLE 74

This Example illustrates the preparation of an oligomer of high molecular weight according to the present invention.

A mixture of diphenyl oxide (42.5 grams), methacrylic acid (130 mls), 85% w/w sulphuric acid (67.6 mls) and water (20 mls) was heated to 65° C. and solution of trioxane (30 grams) in methacrylic acid (50 mls) was added portionwise over 30 minutes. The temperature rose to 70° C. during the addition. The reaction mixture was heated for a further 2.5 hours at 65° C.

The reaction mixture was worked up as in Example 71 to leave an oligomer according to the present invention in the form of a tack-free glass (50 grams); gel permeation chromatography indicated $M_n=1850$ and $M_w=9000$; the functionality was 5.9 and $C^{13}$ nuclear magnetic resonance spectroscopy indicated as ratio of para-para linkages to ortho-para linkages.

EXAMPLES 75–82

The procedure described in Example 74 was repeated using the molar ratios shown in Table 12 for the times and with the results indicated therein.

TABLE 12

| Example No. | Molecular Ratios | | | | | Reaction Time (Hours) | $M_w$ | $M_n$ | Functionality |
|---|---|---|---|---|---|---|---|---|---|
| | A | B | C | D | E | | | | |
| 75 | 1 | 2.26 | 2.2 | 8.00 | 1.50 | 1.00 | 4500 | 2500 | 2.4 |
| 76 | 1 | 1.80 | 3.1 | 8.80 | 1.60 | 1.75 | 1833 | 1027 | 2.2 |
| 77 | 1 | 3.95 | 9.7 | 8.24 | 2.64 | 2.50 | 1271 | 870 | 2.8 |
| 78 | 1 | 3.95 | 10.5 | 8.48 | 3.33 | 3.00 | 1264 | 849 | 2.9 |
| 79 | 1 | 3.95 | 9.6 | 8.48 | 3.33 | 2.75 | 1274 | 875 | 2.6 |
| 80 | 1 | 2.26 | 4.4 | 8.48 | 3.33 | 2.50 | 1310 | 898 | 2.3 |
| 81 | 1 | 2.70 | 4.9 | 8.48 | 4.00 | 2.00 | 1334 | 1017 | 2.9 |
| 82 | 1 | 3.38 | 7.7 | 8.48 | 4.00 | 2.10 | 2568 | 1078 | 3.4 |

A: Diphenyl oxide
B: 85% w/w sulphuric acid
C: Water
D: Methacrylic acid
E: Formaldehyde (in the form of trioxan)

The ratio of para-para linkages to ortho:para linkages was found to be 3.1:1 in Example 82.

EXAMPLE 83

The general procedure described in Examples 14–16 was repeated using diphenyl oxide (1.14 liters), paraformaldehyde (1.8 kilograms), methacrylic acid (8 liters) and sulphuric acid (specific gravity 1.550; 6 liters). The reaction was stopped after 2.75 hours.

The product had $M_n = 878$; a functionality of 4.2; and a para-para:ortho-para ratio of 4.5:1.

EXAMPLE 84

The general procedure described in Examples 14–16 was repeated using diphenyl oxide (28.5 mls), trioxan (22.5 grams), methacrylic acid (200 mls), sulphuric acid (specific gravity 1.550; 150 mls) and water (80 grams). The reaction was stopped after 21 hours.

The product had a ratio of para-para linkages to ortho-para linkages of 4.2:1.

EXAMPLE 85

This Example illustrates the good wear properties of a dental composition according to the present invention.

A dental composition according to the present invention, comprising a preferred three component initiator system, and prepared by thoroughly mixing a portion (64.0 grams) of the oligomer prepared in Example 14, triethylene glycol dimethacrylate (59.1 grams), a borosilicate glass having the particle size distribution indicated in FIG. 2 of U.S. Pat. No. 4,407,984 (428 grams), camphorquinone (0.93 grams), N,N-dimethyl-2-aminoethyl methacrylate (0.63 grams) and t-butyl perbenzoate (1.23 grams) was cured under the conditions described in Example 68.

The cured product had a flexural strength of 101.1±10.1 MPa, a flexural modulus of 12.9±0.7 GPa and a wear depth of 41.8±7.4 microns on an area of 0.191 mm² as determined by the method described in the Journal of Biomedical Materials Research (1975), Volume 9, pages 341–353 at 340,000 cycles under a load of 350 grams with a cusp diameter of 3 mm at 60 cycles/minute.

In a comparative test a known dental composition comprising a vinyl urethane resin (58.35 grams) derived from oxypropylated-bisphenol A, hexamethylenediisocyanate and hydroxyisopropyl methacrylate as described in U.S. Pat. No. 4,407,984, borosilicate glass as hereinbefore described (428 grams), camphorquinone (0.88 grams), N,N-dimethyl-2-aminoethyl methacrylate (0.58 grams) and t-butyl perbenzoate (1.17 grams) was cured as described in Example 68.

Under the conditions hereinbefore described it showed more wear (wear depth 47.3±20.6 microns on an area of 0.239 mm²) than the cured product from the dental composition according to the present invention.

I claim:

1. A dental filling material which comprises
   (a) an oligomer, which may be linear or branched, which
   (i) comprises the repeating unit —Ar¹-CHR— wherein Ar¹ is an aromatic group, or a substituted derivative thereof, each of which aromatic groups may be the same or different and R, each of which may be the same or different, is hydrogen or a hydrocarbyl group;
   (iii) has pendant and/or terminal groups, which may be the same or different; which are acyloxymethyl groups in which the acyl portion is derived from polymerizable olefinically unsaturated carboxylic acid; and
   (iii) has an average functionality between 0.5 and 10; and
   (b) a particulate filler.

2. A fluid dental filling material as claimed in claim 1 comprising a comonomer which is copolymerisable with the oligomer.

3. A dental filling material as claimed in claim 2 wherein the comonomer is an ester of acrylic acid or methacrylic acid.

4. A dental filling material as claimed in claim 3 wherein the ester is a diester of diethylene glycol or triethylene glycol.

5. A dental filling material as claimed in claim 2 wherein the ratio of the oligomer to the copolymerizable monomer is such that the refractive index of the mixture thereof is equal to the refractive index of the particulate filler.

6. A dental filling material as claimed in claim 1 wherein Ar¹ has the structure —φ—Y¹—φ—, wherein φ is the phenylene group and Y¹ is a direct link between two phenylene groups, or a divalent residue which includes one or more in-chain atoms, each of which atoms may be carbon or a hetero atom and may have one or more atoms appendant thereto.

7. A dental filling material as claimed in claim 6 wherein Y¹ is oxygen.

8. a dental filling material as claimed in claim 6 wherein the ratio of para-para linkages to ortho-para linkages is less than 5:1.

9. A dental filling material as claimed in claim 8 in which the said ratio is between 5:1 and 2:1.

10. A dental filling material as claimed in claim 1 wherein R is hydrogen.

11. A dental filling material as claimed in claim 1 wherein the polymerizable olefinically unsaturated carboxylic acid is acrylic acid, methacrylic acid or both.

12. A dental filling material as claimed in claim 1 wherein the functionality is between 2 and 5.

13. A dental filling material as claimed in claim 1 wherein the oligomer has a number average molecular weight between 500 and 1000.

14. A dental filling material as claimed in claim 1 wherein the particulate filler is glass.

15. A dental filling material as claimed in claim 1 comprising a photo-initiator system which is sensitive to visible light.

16. A dental product prepared by curing a dental filling material as claimed in claim 1.

* * * * *